US007932355B2

(12) United States Patent
Chtourou et al.

(10) Patent No.: US 7,932,355 B2
(45) Date of Patent: Apr. 26, 2011

(54) VIRALLY-SAFE FACTOR VIII WITH A LOW CONTENT OF HIGHER MULTIMERS

(75) Inventors: Abdessatar Chtourou, Elancourt (FR); Michel Nogre, Vanves (FR); Roland Schmitthaeusler, Guyancourt (FR)

(73) Assignee: LFB SA, Les Ulis (FR)

( * ) Notice: Subject to any disclaimer, the term of this patent is extended or adjusted under 35 U.S.C. 154(b) by 819 days.

(21) Appl. No.: 10/576,794

(22) PCT Filed: Oct. 25, 2004

(86) PCT No.: PCT/FR2004/002737
§ 371 (c)(1),
(2), (4) Date: May 24, 2007

(87) PCT Pub. No.: WO2005/040214
PCT Pub. Date: May 6, 2005

(65) Prior Publication Data
US 2007/0275880 A1        Nov. 29, 2007

(30) Foreign Application Priority Data

Oct. 23, 2003   (FR) ...................................... 03 12398

(51) Int. Cl.
*A61K 35/14*     (2006.01)
*A23J 1/00*      (2006.01)
*C12N 7/04*      (2006.01)
(52) U.S. Cl. .......................... 530/383; 530/412; 530/414
(58) Field of Classification Search .................. None
See application file for complete search history.

(56) References Cited

U.S. PATENT DOCUMENTS

| 5,522,991 | A | 6/1996 | Tuccelli et al. | |
| 6,967,239 | B1 * | 11/2005 | Chtourou et al. | 530/383 |
| 2003/0232969 | A1 | 12/2003 | Lengsfeld et al. | |
| 2009/0176709 | A1 | 7/2009 | Nieto et al. | |

FOREIGN PATENT DOCUMENTS

| EP | 0 860 444 A1 | 8/1998 |
| EP | 1 270 595 B1 | 1/2003 |
| EP | 1 331 266 A1 | 7/2003 |
| EP | 1 348 445 A1 | 10/2003 |
| EP | 1 443 961 B1 | 8/2004 |
| WO | WO 96/00237 A1 | 1/1996 |
| WO | WO-99/31138 A | 6/1999 |

OTHER PUBLICATIONS

Weinstein, "Immunoaffinity Purification of Factor VIII", Annals Of Clinical and Laboratory Science, vol. 19, No. 2, pp. 84-91, Mar. 1, 1989.
Mentzer et al., "Characterization of factor VIII/von Willebrand factor concentrates using a modified method of von Willebrand factor multimer analysis", Haemophilia, vol. 4, No. 3, pp. 25-32, 1998.
Furuya et al., "Implementation of a 20-nm por-size filter in the plasma-derived Factor VIII manufacturing process", Vox Sanguinis, vol. 19, pp. 119-125, 2006.
Advanced Catalogue Search, ATCC No. CRL-1662, Product Description, [online] [retrieved on Sep. 22, 2009]. Retrieved from the Internet: <URL: mhtml:file://W:\Intellectual Property\APPLICATIONS\OPPOSITIONS\LFB\atcc_crl ...>.
Advanced Catalogue Search, ATCC No. CRL-1823, Product Description [online] [retrieved on Sep. 22, 2009]. Retrieved from the Internet: <URL: http://www.Igcstandards-atcc.org/ LGCAdvancedCatalogueSearch/Product Description...>.
Alberts, et al., Molecular Biology of The Cell, 3$^{rd}$ Ed., p. 1206, Ch. 23: *The Immune System*, Garland Publishing, 1994.
Armstrong-Fisher et al., "Evaluation of a panel of human monoclonal antibodies to D and Exploration of the synergistic effects of blending IgG1 and IgG3 antibodies on their in vitro biologic function," *Transfusion*, Aug. 1999, pp. 1005-1012, vol. 39.
Blood Plasma, Wikipedia, [online] [retrieved on Sep. 22, 2009]. Retrieved from the Internet: <URL: http://en.wikipedia.org/wiki/ Blood_plasma>, 3 pages. Revision history of Blood plasma, Wikipedia, [online] [retrieved Sep. 22, 2009]. Retrieved from the Internet: <URL: http://en.wikipedia.org/w/index.php?title=Blood_ plasma&limit=500&action=history>, 18 pages.
Boyd et al., "The Effect of the Removal of Sialic Acid, Galactose and Total Carbohydrate on the Functional Activity of Campath-1H," *Mole. Immunol.*, 1995, pp. 1311-1318, vol. 32, Nos. 17/18.
Brand, A., "Immunosuppression and Immunomodulation," *Immunological and Infectious Diseases of the Peripheral Nerves*, Latov et al., editors, Cambridge University Press, Chapter 24, pp. 366-368, 1998.
Bredius et al., "Role of neutrophile FcγRIIa (CD32) and FcγRIIIb (CD16) polymorphic forms in phagocytosis of human IgG1- and IgG3-opsonized bacteria and erythrocytes," *Immunology*, 1994, pp. 624-630, vol. 83.
Cant et al., "Glycosylation and functional activity of anti-D secreted by two human lymphoblastoid cell lines," *Cytotechnology*, 1994, pp. 223-228, vol. 15.
Carroll et al., "Mouse X human heterohybridomas as fusion partners with human," *J. Immunol.* Methods, 1986, pp. 61-72, vol. 89, Elsevier.
CD61, Wikipedia, [online] [retrieved on Sep. 22, 2009]. Retrieved from the Internet: <URL: http://en.wikipedia.org/wiki/CD61, 5 pages. Revision history of CD61, [online] [retrieved on Sep. 22, 2009]. Retrieved from the Internet: <URL: http://en.wikipedia.org/ w/index.php?title=CD61&action=history, 1 page.
Chowdhury et al., "Tailor-made antibody therapeutics," *Methods*, 2005, pp. 11-24, vol. 36, Elsevier.
Ducrot et al., "Use of the DAF Assay to Assess the Functional Properties of Polyclonal and Monoclonal Rh D Antibodies," *Vox Sang*, 1996, pp. 30-36, vol. 71.

(Continued)

*Primary Examiner* — Manjunath N Rao
*Assistant Examiner* — Marsha M Tsay
(74) *Attorney, Agent, or Firm* — Foley & Lardner LLP

(57) ABSTRACT

La present invention pertains to a composition of plasma-derived virally-safe factor VIII, obtained after nanometric filtration, said composition comprising von Willebrand factor (vWF) at a rate of 15% or less of decamers and higher multimers. Such compositions have a reduction factor of the virus titre higher than 4 log and are thus suitable for treatment of hemophilia.

5 Claims, No Drawings

OTHER PUBLICATIONS

Galili et al., "A Unique Natural Human IgG Antibody with Anti-α-Galactosyl Specificity," *J. Exp. Med.*, Nov. 1984, pp. 1519-1531, vol. 160.

Goossens, et al., "Human monoclonal antibodies against blood group antigens. Preparation of a series of stable EBV immortalized B clones producing high levels of antibody of different isotypes and specificities," *J. Immunol. Methods*, 1987, pp. 193-200, vol. 101, Elsevier.

Greenman et al., "Comparative efficiencies of bispecific F(ab'γ)₂ and chimeric mouse/human IgG antibodies in recruiting cellular effectors for cytotoxicity via Fcγ receptors," *Cancer Immunol. Immunother*, 1992, pp. 361-369, vol. 34.

Hadley et al., "The functional activity of FcγRII and FcγRIII on subsets of human lymphocytes," *Immunology*, 1992, pp. 446-451, vol. 76.

Hsu et al., "Differential N-Glycan Patterns of Secreted and Intracellular IgG Produced in *Trichoplusia ni* Cells," *J. Biol. Chem.*, Apr. 1997, pp. 9062-9070, vol. 272, No. 14.

Hughes-Jones et al., "Nucleotide sequences and three-dimensional modeling of the $V_H$ and $V_L$ domains of two human monoclonal antibodies specific for the D antigen of the human Rh-blood-group system," *Biochem. J.*, 1990, pp. 135-140, vol. 268.

Ip et al., "Structural Characterization of the N-Glycans of a Humanized Anti-CD18 Murine Immunoglobulin G," *Archives of Biochemistry and Biophysics*, Feb. 1991, pp. 387-399, vol. 208, No. 2.

Jefferis et al., "IgG-Fc-mediated effector functions: molecular definition of interaction sites for effector ligands and the role of glycosylation," *Immunol. Reviews*, 1998, pp. 59-76, vol. 163.

Keler et al., "Bispecific antibody-dependent Cellular Cytotoxicity of HER2/*neu*-overexpressing Tumor Cells by Fcγ Receptor Type I-expressing Effector Cells," *Cancer Research*, Sep. 1997, pp. 4008-4014, vol. 57.

Kilmartin et al., "Rat Monoclonal Antitubulin antibodies Derived by Using a New Nonsecreting Rat Cell Line," *J. Cell Biol.*, Jun. 1982, pp. 576-582, vol. 93.

Klein et al., "Human recombinant anti-Rh(D) monoclonal antibodies: Improvement of biological properties by in vitro class-switch," *Human Antibodies*, 1997, pp. 17-25, vol. 8, No. 1.

Kumpel et al., "Activity and Fcγ receptor utilization of IgG anti-D monoclonal antibodies in monocytes chemiluminescence assays and lymphocyte ADCC assays," 4th Workshop on Mabs against human red blood cells and related antigens, PARIS, Jul. 19-20, 2002, p. 1.

Kumpel et al., "Galactosylation of human IgG monoclonal anti-D produced by EBV-transformed By-lymphoblastoid cell lines is dependent on culture method and affects Fc receptor-mediated functional activity," *Hum. Antibod. Hybridomas*, 1994, pp. 143-151, vol. 5, Nos. 3 and 4.

Kumpel et al., Heterogeneity in the ability of IgG1 monoclonal anti-D to promote lymphocyte-mediated red cell lysis, *Eur. J. Immunol.*, 1989, pp. 2283-2288, vol. 19.

Kumpel et al., "Human Rh D monoclonal antibodies (BRAD-3 and BRAD-5) cause accelerated clearance of Rh D+ red blood cells and suppression of Rh D immunication in Rh D- volunteers," *Blood*, 1995, pp. 1701-1709, vol. 86, American Society of Hematology.

Kumpel, B.M., "Efficacy of RhD monoclonal antibodies in clinical trials as replacement therapy for prophylactic anti-D immunoglobulin: more questions than answers," *Vox Sang.*, 2007, pp. 99-111, vol. 93.

Kumpel, B.M., "Monoclonal anti-D for prophylaxis of RhD haemolytic disease of the newborn," *Transfus. Clin. Biol.*, 1997, pp. 351-356, vol. 4.

Lifely et al., "Glycosylation and biological activity of CAMPATH-1H expressed in different cell lines and grown under different culture conditions," *Glycobiology*, 1995, pp. 813-822, vol. 5, No. 8.

Lund et al., "Control of IgG/Fc Glycosylation: A Comparison of Oligosaccharides from Chimeric Human/Mouse and Mouse Subclass Immunoglobulin Gs," *Mole. Immunol.*, 1993, pp. 741-748, vol. 30, No. 8.

Melamed et al., "Requirements for the establishment of heterohybridomas secreting monoclonal human antibody to rhesus (D) blood group antigen," *J. Immunol. Methods*, 1987, pp. 245-251, vol. 104, Elsevier.

Merriam-Webster, Webster's Third New International Dictionary of the English Language Unabridged, 1961, p. 1761.

Mori et al., "Non-fucosylated therapeutic antibodies: the next generation of therapeutic antibodies," *Cytotechnology*, 2007, pp. 109-114, vol. 55.

Nakamura et al., "Chimeric Anti-Ganglioside $G_{M2}$ Antibody with Antitumor Activity," *Cancer Research*, Mar. 1994, pp. 1511-1516, vol. 54.

Papac et al., "A high-throughput microscale method to release N-linked oligosaccharides from glycoproteins for matrix-assisted laser desorption/ionization time-of-flight mass spectrometric analysis," 1998, pp. 463-472, vol. 8, No. 5.

Paterson et al., "Variation in IgG1 heavy chain allotype does not contribute to differences in biological activity of two human anti-Rhesus (D) monoclonal antibodies," *Immunotechnology*, 1998, pp. 37-47, vol. 4, Elsevier.

Presta, Leonard G., "Engineering of therapeutic antibodies to minimize immunogenicity and optimize function," *Advanced Drug Delivery Reviews*, 2006, pp. 640-656, vol. 58, Elsevier.

Puthalakath et al., "Glycosylation Defect in Lec1 Chinese Hamster Ovary Mutant Is Due to a Point Mutation in N-Acetylglucosaminyltransferase I Gene," *J. Biol. Chem.*, Nov. 1996, pp. 27818-27822, vol. 271, No. 44.

Raju et al., "Species-specific variation in glycosylation of IgG: evidence for the species-specific sialylation and branch-specific galactosylation and importance for engineering recombinant glycoprotein therapeutics," *Glycobiology*, 2000, pp. 477-486, vol. 10, No. 5.

Revillard, Jean-Pierre, *Immunologie*, 2d Ed., 1995, various chapters, DeBoeck Université.

Rothman et al., "Antibody-dependent Cytotoxicity Mediated by Natural Killer Cells is Enhanced by Castanospermine-induced Alterations of IgG Glycosylation," *Mole. Immunol.*, 1989, pp. 1113-1123, vol. 26, No. 12.

Segal et al., "The Role of Non-immune IgG in Controlling IgG-Mediated Effector Functions," *Mole. Immunol.*, 1983, pp. 1177-1189, vol. 20, No. 11.

Shaw et al., "Human Lymphocyte, Monocyte, and Neutrophil Antibody-Dependent Cell-Mediated Cytotoxicity toward Human Erythrocytes," *Cell. Immunol.*, 1978, pp. 122-133, vol. 41.

Shields et al., "Lack of Fucose on Human IgG1 N-Linked Oligosaccharide Improves Binding to Human FcγRIII and Antibody-dependent Cellular Toxicity," *J. Bio. Chem.*, Jul. 2002, pp. 26733-26740, vol. 277, No. 30.

Shinkawa et al., "The Absence of Fucose but Not the Presence of Galactose or Bisecting N-Acetylglucosamine of Human IgG1 Complex-type Oligosaccharides Shows the Critical Role of Enhancing Antibody-dependent Cellular Cytotoxicity," *J. Biol. Chem.*, Jan. 2003, pp. 3466-3473, vol. 278, No. 5.

Shitara et al., "A new vector for the high level expression of chimeric antibodies in myeloma cells," *J. Immunol. Methods*, 1994, pp. 271-278, vol. 167, Elsevier Science B.V.

Sibéril et al., "Selection of a human anti-RhD monoclonal antibody for therapeutic use: Impact of IgG glycosylatiion on activating and inhibitory FcγR functions," *Clinical Immunol.*, 2006, pp. 170-179, vol. 118, Elsevier.

Takahashi et al., "Comparative Structural Study of the N-Linked Oligosaccharides of Human IgG Normal and Pathological Immunoglobulin G," *Biochemistry*, 1987, pp. 1137-1144, vol. 26.

Tandai et al., "Structural Study of the Sugar Moieties of Monoclonal Antibodies Secreted by Human-Mouse Hybridoma," *Archives of Biochemistry and Biophysics*, Dec. 1991, pp. 339-348, vol. 291, No. 2.

Teillaud, Jean-Luc, "Engineering of monoclonal antibodies and antibody-based fusion proteins: successes and challenges," *Expert Opin. Biol. Ther.*, 2005, pp. S15-S27, vol. 5, Suppl. 1, Ashley Publications.

Umaña et al., "Engineered glycoforms of an antineuro-blastoma IgG1 with optimized antibody-dependent cellular cytotoxic activity," *Nature Biotechnology*, Feb. 1999, pp. 176-180, vol. 17.

Urbaniak et al., "Prediction of the Outcome of Rhesus Haemolytic Disease of the Newborn: Additional Information Using an ADCC Assay," *Vox Sang.*, 1984, pp. 323-329, vol. 46.

Urbaniak, S.J., "ADCC (K-Cell) Lysis of Human Erythrocytes Sensitized with Rhesus Alloantibodies," *British J. Haematology*, 1979, pp. 303-314, vol. 42.

Wright et al., Effect of Altered $C_H2$-associated Carbohydrate Structure on the Functional Properties and In Vivo Fate of Chimeric Mouse-Human Immunoglobulin G1, J. Exp. Med., Sep. 1994, pp. 1087-1096, vol. 180, The Rockefeller University Press.

Wright et al., "Effect of C2-Associated Carbohydrate Structure on Ig Effector Function: Studies with Chimeric Mouse-Human IgG1 Antibodies in Glycosylation Mutants of Chinese Hamster Ovary Cells," *J. of Immunol.*, 1998, pp. 3393-3402.

Wright et al., "Effect of glycosylation on antibody function: implications for genetic engineering," *TIBTECH*, Jan. 1997, pp. 26-32, vol. 15.

Wright et al., "In vivo Trafficking and catabolism of IgG1 antibodies with Fc associated carbohydrates of differing structure," *Glycobiology*, 2000, pp. 1347-1355, vol. 10, No. 12.

Yano et al., "Analysis of N-linked oligosaccharides in the Fc region of an antibody," Experiment Summary, 16 pages, Jun. 23 to Jul. 28, 2009.

Kriezek et al., "A Rapid Method to Visualize von Willebrand Factor Multimers by Using Agarose Gel Electrophoresis, Immunolocalization and Luminographic Detection," *Thrombosis Research*, vol. 97, pp. 457-462, 2000.

Burnouf-Radosevich et al., "Nanofiltration, a New Specific Virus Elimination Method Applied to High-Purity Factor IX and Factor XI Concentrates," *Vox Sang*, vol. 67, pp. 132-138, 1994.

Feldman et al., "Improved Safety from Plasma Derivatives: Purification and Viral Elimination Characteristics of Mononine," *Acta Haematol.*, vol. 94 (suppl.), pp. 25-34, 1995.

Burnouf et al., "Nanofiltration of plasma-derived biopharmaceutical products," *Haemophilia*, vol. 9, pp. 24-37, 2003.

\* cited by examiner

VIRALLY-SAFE FACTOR VIII WITH A LOW CONTENT OF HIGHER MULTIMERS

The present invention relates to a plasma-derived, virally-safe Factor VIII composition obtained after nanometric filtration, whose von Willebrand Factor content (vWF) is 15% or less of decamers and higher multimers. Such compositions show a reduction of virus titre by a factor that is higher than 4 log, and are therefore suitable for treating haemophilia.

The availability of coagulation factor has been a public health problem for some time. To meet demand, industrialists have developed techniques for producing recombinant factors and it was thought that over the longer term these would take over from production using plasma pools. However the quantities produced still appear to be unsatisfactory and investments for developing these products are fairly considerable. Also an immunity reaction against these recombinant factors is seen in some patients, which implies the administering of a high dose to arrive at the desired therapeutic effect. Finally, some patients do not tolerate recombinant factors.

Therefore the production of plasma-derived coagulation factors remains a major challenge.

Factor VIII or anti-haemophilia factor is a plasma protein present in small concentrations in human plasma. This factor catalyses biochemical reactions of blood coagulation by increasing the reaction rate to lead to the formation of a clot of haemostatic fibrin obtained from soluble fibrinogen subjected to the action of thrombin in the presence of calcium. Factor VIII takes part in the series of reactions leading to thrombin formation which is the enzymatic activity responsible for converting fibrinogen into fibrin. The central point of coagulation therefore lies in the presence and activation of FVIII.

Haemophilic persons, who are FVIII deficient, are treated by injection of these purified FVIIIs obtained either by genetic recombination or by extraction from human plasma.

In the latter case, methods for virus inactivation and/or removal must be applied to protect haemophilia patients treated with these concentrates against any infection due to viruses transmissible by blood or its derivatives: hepatitis A, B, C viruses, HIV or Parovirus B19.

Therefore one of the essential problems related to the preparation of Factor VIII from plasma lies in the need to inactivate and/or remove viruses originally contained in the blood, at least in accordance with laid down standards, whilst maintaining an optimum Factor yield after preparation. Numerous virus inactivation techniques have therefore been developed, such as dry heating, pasteurising, solvent-detergent treatment. All these techniques are relatively effective against enveloped viruses but the inactivation or removal of non-enveloped viruses, in particular small viruses such as Parovirus B19 or hepatitis A virus, form a major obstacle.

More recent technologies use the virus retaining capacities of membranes of small pore size. These technologies indeed show remarkable efficacy against small-size viruses such as Parovirus B19 or hepatitis A virus, and can be applied to proteins of low molecular weight. However the cut-off thresholds used, less than 900 kD, exclude considering the filtration of high molecular weight proteins or protein complexes such as Factor VIII without a major yield loss.

Factor VIII is a complex edifice of an active protein, FVIII, carried by a protein of high molecular weight to which FVIII is bound by ionic and hydrophobic bonds. This high molecular weight protein is the von Willebrand Factor (vWF) consisting of a group of elementary monomers of varying multimerisation leading to tetramer-assembled structures and even up to structures containing more than sixteen monomers.

Depending upon the FVIII purification methods used, the end product may contain vWF at varying degrees of multimerisation (METZNER, HERMENTIN et al—Haemophilia (1998), 4 (Suppl. 3), 25-32.

Yet in our patent FR 97 15888 we described how it is possible to filter plasma-derived FVIII, despite its size, while retaining viruses 20 nm or greater in size, through filters having an approximate porosity of 15 nm with a chaotropic ion concentration of at least 0.2M.

More recently, research conducted to improve this method and to choose different types of filter materials has shown that filter pore size and technical limits may vary from one manufacturer to another. It therefore appeared necessary to find a quick, reproducible test with which it is possible to verify that the end product does meet health requirements.

The assurance that viruses have been removed by filtering is guaranteed by validation methods made on the filter after the FVIII solution has been passed. These methods may entail measurement of gaseous diffusion through the membrane for example or, for cuprophane filters, measurement of calibrated colloidal gold particles passing through the filter.

But no method refers to the actual filtered product itself to determine whether or not it has undergone filtration able to retain viruses within laid down limits.

A finer analysis of the composition of FVIII multimers before and after filtration was conducted, at the same time as measurement of the reduction in virus titre provided by filtration of Factor VIII.

In surprising, unexpected manner we have found that the reduction of high molecular weight vWF multimers, measured in the filtrates of FVIII, correlates with the efficacy of virus retention by the filter. In addition, by verifying multimer content, we have discovered that it is possible to filter at approximately 20 nm. We therefore propose a new means for the high yield production and characterisation of FVIII which meets the requirements of virus removal by nanometric filtration.

DESCRIPTION

According to a first characteristic the present invention concerns a plasma-derived, pharmaceutical Factor VIII composition whose viral safety corresponds to a reduction factor of more than 4 log, which meets safety requirements for virus removal by filtration. The FVIII composition made virally safe is characterized by a low residual content of high-multimerisation vWF.

More specifically the invention concerns a plasma-derived Factor VIII composition, obtained after filtering through a nanometric filter of nominal pore size 15±2 nm to 23±2 nm, characterized in that its content of von Willebrand Factor (vWF) is 15% or less of decamers and higher multimers. In this composition, the titre of a virus of size 27±3 nm is reduced by a factor of 4 log or more, preferably 5 log, advantageously 6 log compared with the solution before filtration.

This composition may be in the form of an injectable solution by intravenous, intramuscular or subcutaneous route for example.

The invention also concerns the correlation between the presence of no more than 15% decamers and higher multimers of vWF and a virus titre reduction factor of at least 4 log.

Therefore, according a second characteristic, the invention concerns a method for testing the viral safety of a plasma-derived Factor VIII composition, said method comprising a step consisting of determining the residual content of high multimerisation vWF. In particular it will be considered that a composition is virally safe if less than 15% vWF decamers and higher multimers is detected.

According to an additional characteristic, the invention relates to a test kit which can be used to implement the above-mentioned method, containing the necessary reagents for assay of vWF multimers whose multimerisation is 10 or over.

The invention also concerns a method for preparing a virally-safe Factor VIII solution comprising a filtering step through nanometric filters of nominal pore size 15±2 nm to 23±2 nm, i.e. a range of 13 nm to 25 nm, and an assay step of von Willebrand Factor (vWF) decamers and higher multimers. The assay step preferably consists of verification that the content of vWF decamers and higher mutimers is no more than 15%. For example, a sample is subjected to gel electrophoresis to separate the multimers per size. The multimers are visualized using a I-125 labelled anti-vWF antibody or other labeller. The light intensity of each strip, each corresponding to a vWF multimer, is determined and the limit content of higher multimer is calculated. Rabbit anti-vWF can also be used (Darko Corp, USA) and a second rabbit anti-Ig antibody conjugated with horseradish peroxidase (HRP), the multimers being visualized using a commercially available chemiluminescent kit (ECL detection kit, Amersham Pharmacia) to detect HRP on Western blots.

On completion, Factor VIII solutions are obtained whose factor of virus titre reduction, for a virus of size 27±3 nm, is 4 log or more, preferably 5 log, advantageously 6 log. Before filtration the Factor VIII solution optimally comprises a chaotropic ion, $CaCl_2$ for example, at a concentration of 0.2 M or over, for example 0.25 or 0.35 M.

The invention also concerns the use of a composition as mentioned above to prepare a medicinal product intended for the treatment of diseases related to blood coagulation, haemophilia in particular.

Example 1

Method for Preparing Safe FVIII by Filtering Through a 15 nm Nanometric Filter, and Verification of >10 Multimerisation vWF Content The viruses tested are Phi X 174 bacteriophages, non-enveloped viruses, of diameter 27±3 nm.

Virus culture and assay is conducted in accordance with AFNOR norm NF T 72-181.

The FVIII is collected on leaving the Toyopearl DEAE column and brought to pH6; the $CaCl_2$ concentration is brought to 0.35 M. The temperature of the solution and filter is thermo-regulated at 35° C. and filtering pressure is adjusted to less than 100 mbar.

Under these conditions, the flow rate is 1.2 l/h per $m^2$.

FVIII: C yield is approximately 70% with respect to the FVIII: C before filtration. Table I below gives the distribution of vWF multimers:

TABLE I

| Distribution of multimers (Planova ® 15N) | | |
|---|---|---|
| vW Factor | Before filtering | After filtering |
| <pentamers | 41% | 53% |
| 5 to 9 mers | 34% | 34% |

TABLE I-continued

| Distribution of multimers (Planova ® 15N) | | |
|---|---|---|
| vW Factor | Before filtering | After filtering |
| 10 to 15 mers | 15% | 9% |
| 16 mers and + | 11% | 4% |

A significant reduction in decamers/pentadecamers is found: distribution falls from 15% to 9%.

For hexadecamers and over, the reduction is even more significant: from 11% to 4%.

Assay of Phi X 174 viruses shows a reduction of 6 log on filtration.

Example 2

Method for Preparing Safe FVIII by Filtering Through a 20 nm Nanometric Filter and Verification of >10 Multimerisation vWF Content Filtering is made through a filter of similar type (cuprophane, Planova) but of different porosity (20 to 22 nm), the FVIII solution obtained as in Example 1 is adjusted to pH6 and 0.45 M $CaCl_2$ is added. Pressure is adjusted to 17 mbar and the solution and filter assembly is thermo-regulated at 35° C.

Under these conditions the flow rate is 1.2 l/h per $m^2$ and the FVIII yield is 80% with respect to the initial FVIII.

Table II below gives the composition of vWF multimers:

TABLE II

| distribution of vWF multimers (Planova P21). | | |
|---|---|---|
| vW Factor | Before filtering | After filtering |
| <pentamers | 47% | 56% |
| 5 to 9 mers | 32% | 34% |
| 10 to 15 mers | 13% | 10% |
| 16 mers and + | 11% | 2% |

The decamers-pentadecamers are significantly reduced falling from 13% to 10%.

The hexadecamers are drastically reduced from 11% to 2%.

The reduction factor of virus titre is 4.3 log.

Example 3

High Pressure Filtration Through a Porosity of Approximately 20 nm

For the purpose of examining the performance of the Planova 21 filter under higher pressure conditions and at room temperature, the FVIII solution is adjusted to pH6 and $CaCl_2$ concentration is brought to 0.35 M. The temperature is 22° C. and the pressure is adjusted to 400 mbar.

Under these conditions, the filtering rate reaches 0.5 l/h per $m^2$ and the Factor VIII yield is 64% with respect to the starting product.

Table III gives the vWF multimer composition:

TABLE III

Distribution of vWF multimers (Planova 21 at high pressure)

| vWF multimers | Before filtering | After filtering |
|---|---|---|
| <5 mers | 44% | 50% |
| 5 to 9 mers | 34% | 35% |
| 10 to 15 mers | 13% | 8% |
| 16 mers and + | 10% | 7% |

The decamers-pentadecamers are reduced from 13% to 8%.

The hexadecamers and higher are reduced from 10% to 7%.

The reduction factor of virus titre is 6.1 log.

Example 4

Test on a Filter of 20 nm Polysulfone Type at high Pressure

For the purpose of validating another type of filter, a FVIII filter test was conducted on a filter of type polysulfone DV20 (Pall). This type of filter tolerates higher pressures than cuprophane filters. Therefore Example 3 was set up to evaluate the performance of the cuprophane filter at higher pressure in order to collect observations under similar conditions.

The FVIII solution is brought to pH6 in the presence of 0.35 M $CaCl_2$. The solution and filter are thermo-regulated at 35° C. The pressure required to operate the filter is 950 mbar. Under these conditions the mean flow rate is 7 l/h per m2.

The Factor VIII yield is 70% with respect to initial FVIII.

Table IV gives the vWF multimer composition.

TABLE IV

Distribution of vWF multimers (DV20 Pall, polysulfone)

| vWF multimers | Before filtering | After filtering |
|---|---|---|
| <5 mers | 35% | 53% |
| 5 to 9 mers | 38% | 30% |
| 10 to 15 mers | 27% | 12% |
| 16 mers and + | 10% | 6% |

The hexadecamers undergo a drastic reduction from 10% to 6%

However, virus titre reduction is only 2.1 log which is far below the norm fixed by regulatory authorities (>4 log) to demonstrate the efficacy of a virus elimination method for the purpose of reducing the potential viral content of a product derived from human plasma.

CONCLUSION

Table V groups together the sum of multimer values from the decamer. It is found that: when the sum of vWF decamers and higher multimers is no more than 15%, the reduction in virus titre is always >4 log.

On the other hand, if this sum exceeds 16%, the reduction in viral titre is less than 4 log.

This correlation between vWF multimers of order 10 and higher and virus presence is probably related to filter passing phenomena according to conditions of filtration, porosity, type of filtering materials, filter texture, pore geometry. All these parameters may have an influence on the retaining or non-retaining of viruses. The tests applied to the filter, after use, give an indication of its efficacy but it is only in the case of the invention that the filtered product, Factor VIII accompanied by FVIII multimers characterized according to their extent of multimerisation, that the assurance of efficient filtering for virus retention can be given.

The virus retention efficacy of >4 log is therefore related to a distribution of vWF multimers in the filtrate of no more than 15% multimers of multimerisation>10. These data are summarized in Table V:

TABLE V

Correlation between viral reduction factor (Rf) and >10 mer vWF multimer composition.

| | Example 1 | | Example 2 | | Example 3 | | Example 4 | |
|---|---|---|---|---|---|---|---|---|
| | Before | After | Before | After | Before | After | Before | After |
| Multimers 10-15 | 15% | 9% | 13% | 10% | 13% | 8% | 27% | 12% |
| Multimers 16+ | 11% | 4% | 10% | 2% | 10% | 7% | 10% | 6% |
| Total | 26% | 13% | 23% | 12% | 23% | 15% | 37% | 18% |
| Virus reduction factor (log) | 6.0 | | 4.3 | | 6.1 | | 2.1 | |

The invention claimed is:

1. A method for preparing a virally safe Factor VIII solution, the method comprising:
    filtering a solution comprising Factor VIII through nanometric filters having a pore size of 13 nm to 25 nm;
    assaying the filtrate to determine the residual content of high multimerization von Willebrand Factor (vWF); and
    wherein the content of vWF hexadecamers and higher multimers is at least 2% in the filtrate.

2. The method of claim 1, wherein the step of assaying the filtrate includes verifying that the content of vWF decamers and higher multimers is 15% or less.

3. The method of claim 1, wherein a vWF decamer and higher multimer content of 15% or less indicates that the titre reduction factor of a virus having a size diameter of 24 nm to 30 nm is 4 log or more, to about 6 log as compared with the solution before filtration.

4. The method of claim 1, wherein a vWF decamer and higher multimer content of 15% or less indicates that the titre reduction factor of a virus having a size of 24 nm to 30 nm is 5 log or more, to about 6 log as compared with the solution before filtration.

5. The method of claim 1, wherein a vWF decamer and higher multimer content of 15% or less indicates that the titre reduction factor of a virus having a size of 24 nm to 30 nm is about 6 log as compared with the solution before filtration.

* * * * *